United States Patent [19]
Partridge et al.

[11] Patent Number: 4,594,340
[45] Date of Patent: Jun. 10, 1986

[54] 25,26-DEHYDRO-1α,24R-DIHYDROXY-CHOLECALCIFEROL AND 25,26-DEHYDRO-1α,24S-DIHYDROXY-CHOLECALCIFEROL AND THE EPIMERIC MIXTURE

[75] Inventors: John J. Partridge, Upper Montclair; Shian-Jan Shiuey, Nutley; Gary A. Truitt, Passaic; Milan R. Uskokovic, Upper Montclair, all of N.J.

[73] Assignee: Hoffmann-La Roche Inc., Nutley, N.J.

[21] Appl. No.: 676,121

[22] Filed: Nov. 29, 1984

[51] Int. Cl.$^4$ .............................................. C07J 9/00
[52] U.S. Cl. .................................. 514/167; 260/397.2
[58] Field of Search ...................... 260/397.2; 514/167

[56] References Cited
U.S. PATENT DOCUMENTS 4,344,888  8/1982  Takayama et al. ............. 260/397.2
4,391,802  7/1983  Suda et al. ...................... 260/397.2
4,517,125  5/1985  Takayama et al. ............. 260/397.2

OTHER PUBLICATIONS

Frampton, R. J. et al., *Cancer Research*, 42:1116–1119, 1982.
Colston, K. et al, *Cancer Research*, 42:856–859, 1982.
Shiina, Y. et al, *Archives of Biochemistry & Biophysics*, 220:90–94, 1983.
McCarthy, D., *Exp. Hematol,* 11 (Supplement 14): 200, 1983.
Abe, E. et al, *Proceedings of the National Academy of Science,* 78:4990–4994, 1981.
Honma, Y. et al, *Proceedings of the National Academy of Science,* 80:201–204, 1983.
Dokoh, S. et al, *Endocrinology,* 112:200–206, 1983.
Murao, S., *Cancer Research,* 43(8):4989–4996, 1983.
Reitsma et al, *J. Cell Biol.,* 97(5): 347a, 1983.
Rigby, W. F. C. et al, *Blood,* 62(5): 153a 1983.
Olsson et al., *Cancer Research,* 43(12) 5862–5867, 1983.
Eisman, J. A. et al, *Lancet,* Dec. 22/29: 1335–1336, 1979.
Sato, T. et al, *Tohoku J. Exp. Med.,* 138:445–446, 1982.
McCarthy, D. M. et al, *Lancet,* Jan. 14:78–80, 1984.
Sher et al, *Biochem. Journal* (1981) 200, 315–320.
Frampton et al, *Cancer Research,* 43, 4443–4447, 1983.
Koeffler, H. P. et al, *Cancer Research,* 44, 5624–5628, Dec. 1984.

*Primary Examiner*—Elbert L. Roberts
*Attorney, Agent, or Firm*—Jon S. Saxe; Bernard S. Leon; Matthew Boxer

[57] ABSTRACT

The syntheses of 25,26-dehydro-1α,24R-dihydroxycholecalciferol and 25,26-dehydro-1α,24S-dihydroxycholecalciferol and the epimeric mixture which are useful as differentiation inducing agent and anti-proliferation agents are described. 25,26-dehydro-1α,24R-dihydroxycholecalciferol, 25,26-dehydro-1α,24S-dihydroxycholecalciferol, and the epimeric mixture are useful in treating osteoporosis, tumors and leukemia.

12 Claims, No Drawings

25,26-DEHYDRO-1α,24R-DIHYDROXY-CHOLECALCIFEROL AND 25,26-DEHYDRO-1α,24S-DIHYDROXY-CHOLECALCIFEROL AND THE EPIMERIC MIXTURE

BRIEF DESCRIPTION OF THE INVENTION

The invention relates to the compounds 25,26-dehydro-1α,24R-dihydroxycholecalciferol, 25,26-dehydro-1α,24S-dihydroxycholecalciferol and the epimeric mixture. The invention also relates to a synthesis of 25,26-dehydro-1α,24R-dihydroxycholecalciferol, 25,26-dehydro-1α,24S-dihydroxycholecalciferol and the epimerix mixture. 25,26-Dehydro-1α,24R-dihydroxycholecalciferol, 25,26-dehydro-1α,24S-dihydroxycholecalciferol and the epimeric mixture are useful as in treating osteoporosis and as antitumor agents.

DETAILED DESCRIPTION OF THE INVENTION

As used throughout the specification and the appended claims the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, i-propyl, tert-butyl, hexyl, heptyl, octyl and the like. The term "lower alkylene" denotes a divalent substituent consisting solely of carbon and hydrogen of from 1 to 8 carbon atoms which may be straight- or branched chain and whose free valences are attached to two distinct groups. Examples of alkylene groups are methylene, ethylene, propylene, butylene, amylene, hexylene, heptylene, octylene and the like.

The term "substituted" as applied to "phenyl" refers to phenyl which is substituted with one or more of the following groups: alkyl, halogen (that is, fluorine, chlorine, bromine or iodine), nitro, cyano, trifluoromethyl and the like. The term "aralkyl" denotes a radical in which one hydrogen of the alkyl portion of the molecule is substituted by an aryl group. Exemplary of aralkyl are benzyl, phenylethyl, phenylpropyl and the like. The term "aryl" denotes an organic radical derived from an aromatic hydrocarbon by the removal of a hydrogen atom. Exemplary of aryl are phenyl and substituted phenyl. The term "alkanoyl" denotes the residue of an aliphatic carboxylic acid of from 1 to 8 carbon atoms formed by the removal of hydroxyl from the carboxyl group. Exemplary of alkanoyl are acetyl, propionyl, butyroyl, pentanoyl and the like. The term "aralkanoyl" denotes an alkanoyl radical in which one hydrogen of the alkyl portion of the molecule has been substituted by aryl. Exemplary of aralkanoyl are phenylacetyl, phenylpropionyl, phenylbutyroyl, phenylpentanoyl and the like. The term "aroyl" denotes the residue of an aromatic carboxylic acid of from 7 to 20 carbon atoms formed by the removal of a hydroxy group from the carboxyl group. Exemplary of aroyl are benzoyl, toluoyl and the like. The term "acyl" denotes aroyl, aralkanoyl, and alkanoyl.

In the formulas presented herein, the various substituents are illustrated as joined to the steroid nucleus by one of the following notations: a solid line ( ━■ ) indicating a substituent which is above the plane of the molecule), a dotted line (------) indicating a substituent which is below the plane of the molecule, or a wavy line (∿∿∿) indicating a substituent which may be above or below the plane of the molecule. The formulas have all been drawn to show the compounds in their absolute stereo-chemical configuration. Since the starting materials are compounds whose stereochemical configurations are known, the products exist in the single absolute stereochemical configurations described herein. As described below, one may begin the synthesis of the invention, with either 24R- or 24S-epimer of 1α,24,25-trihydroxycholecalciferol or with a mixture of 24R and 24S-epimeric 1α,24,25-trihydroxycholecalciferol in order to prepare either the 24R or 24S-epimer of 25,26-dehydro-1α,24-dihydroxycholecaliciferol, or a mixture of 24R and 24S-epimeric, 25,26-dehydro-1α,24-dihydroxycholecalciferol. The mixture of 24R and 24S-epimers 25,26-dehydro-1α,24-dihydroxycholecalciferol may be designated 25,26-dehydro-1α,24(R,S)-dihydroxycholecalciferol.

The Greek letter xi (ξ) in the name of a vitamin $D_3$ intermediate or metabolite indicates that the stereochemistry of the substituent to which it refers is undefined or that the product consists of a mixture of compounds epimeric at the designated position.

The invention relates to the compounds 25,26-dehydro-1α,24R-dihydroxycholecalciferol and 25,26-dehydro-1α,24S-dihydroxycholecalciferol, and 25,26-dehydro-1α,24(R,S)-dihydroxycholecalciferol; and their synthesis from the substances 1α,24R,25-trihydroxycholecalciferol; 1α,24S,25-trihydroxycholecalciferol and 1α,24(R,S),25-trihydroxycholecalciferol which are all known or can be prepared per known procedures. The synthesis involves as key steps the selective protection of the 1,3,24-hydroxy groups, and the selective dehydration of the 25-hydroxy group to give 25,26-olefins.

In Reaction Scheme I which follows, syntheses of 25,26-dehydro-1α,24R-dihydroxycholecalciferol, 25,26-dehydro-1α,24S-dihydroxycholecalciferol and the epimeric mixture are set forth.

Reaction Scheme 1

Synthesis of 25,26-dehydro-1α,24R—dihydroxycholecalciferol, 25,26-dehydro-1α,24S—dihydroxycholecalciferol and the epimeric mixture

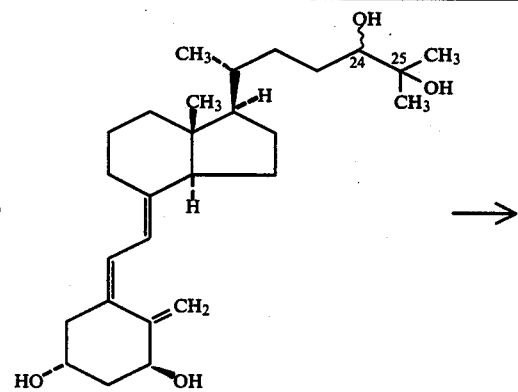

1

-continued
Reaction Scheme 1

Synthesis of 25,26-dehydro-1α,24R—dihydroxycholecalciferol, 25,26-dehydro-1α,24S—dihydroxycholecalciferol and the epimeric mixture

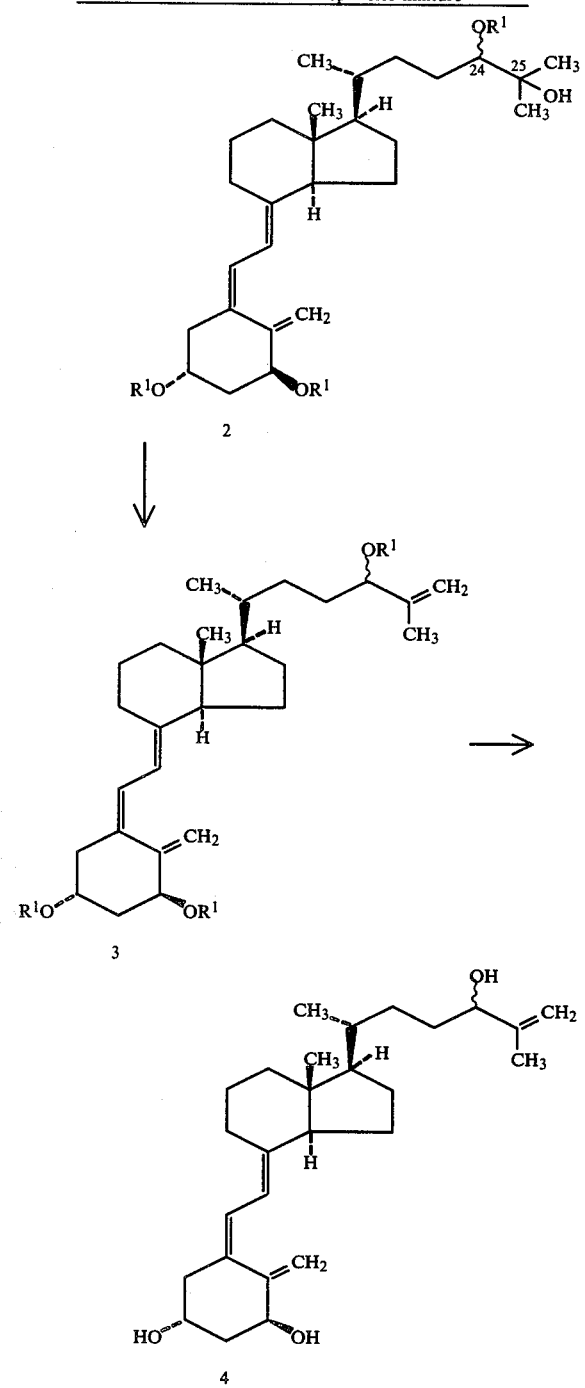

wherein $R^1$ is

wherein $R^2$ is lower alkyl, aralkyl, phenyl, or substituted phenyl; or $R^1$ is lower alkyl, aralkyl, phenyl, substituted phenyl, tri-lower alkylsilyl, di-lower alkylaryl-silyl, lower alkyldiarylsilyl, triarylsilyl or a group of the formula

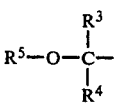

wherein $R^3$ is hydrogen or lower alkyl; $R^4$ and $R^5$ each independently are lower alkyl or $R^4$ and $R^5$ taken together are lower alkylene of from 3 to 6 carbon atoms.

A detailed description of Reaction Scheme 1 now follows.

All of the reactions which are described below are conducted in an inert atmosphere such as, for example, nitrogen or more preferably argon.

The starting material for the process of the invention is a compound of formula 1 that is 1α,24R,25-trihydroxycholecalciferol, the 24S epimer, or the epimeric mixture. As has been noted above, each of these compounds is a known compound or can be prepared by known procedures.

In the description which follows, the transformation of a compound of formula 1 to the corresponding compound of formula 2, 3, and then 4 is set forth. For example, when 1α,24R,25-trihydroxycholecalciferol is used as the compound of formula 1, the corresponding 24R-epimer of formula 2, 3 and 4 result.

A compound of formula 1 can be acylated at the 1-, 3- and 24-positions to obtain a compound of formula 2 by reaction with an acylating agent.

The acylating agent can be a carboxylic acid halide, such as an alkyl carboxylic acid halide, an aralkyl carboxylic acid halide, or an aryl carboxylic acid halide. Exemplary of alkyl carboxylic acid halides are propionyl chloride, or, more preferably, acetyl chloride. Exemplary of aralkyl carboxylic halides are phenylpropionyl chloride, or more preferably, phenylacetyl chloride. Exemplary of aryl carboxylic halides are naphthoyl chloride, or, more preferably, benzoyl chloride.

The carboxylic acid halide employed can be dissolved in the corresponding carboxylic acid or in a solution of a basic salt of the carboxylic acid in the carboxylic acid. For example, the acylating agent can be acetyl chloride in acetic acid or acetyl chloride in a solution of sodium acetate and acetic acid.

The acylating agent can also be a carboxylic acid anhydride such as an alkyl carboxylic acid anhydride, an alkaryl carboxylic acid anhydride, or an aryl carboxylic acid anhydride. Exemplary of alkyl carboxylic acid anhydrides are propionic anhydride, or most preferably acetic anhydride. Exemplary of aralkyl carboxylic acid anhydrides are phenylpropionic anhydride, or, more preferably, phenylacetic anhydride. Exemplary of aryl carboxylic acid anhydrides are naphthoic anhydride, or, more preferably, benzoic acid anhydride.

The carboxylic acid anhydride employed can be dissolved in a corresponding carboxylic acid or in a solution of a basic salt of the carboxylic acid in the carboxylic acid. For example, acetic anhydride can be dissolved in acetic acid or in a solution of sodium acetate dissolved in acetic acid.

The solvent for acylation reaction is a basic solvent, and can be a tertiary alkyl amine such as diisopropylethylamine, or, more preferably, triethylamine; or a tertiary aromatic amine such as lutidine, or most preferably pyridine.

The acylation can be conducted in the presence of a neutral co-solvent such as, for example, a hydrocarbon such as for example, hexane or pentane. The neutral co-solvent can also be an aromatic hydrocarbon such as benzene or toluene. The neutral co-solvent can also be, for example, a chlorinated hydrocarbon such as methylene chloride or 1,2-dichloroethane. The neutral co-solvent can also be a mixture of any of the above listed hydrocarbons, aromatic hydrocarbons and chlorinated hydrocarbons. For example, the neutral co-solvent can be a mixture of hexane and benzene.

The temperature for the acylation reaction can be from about −20° to about 50°, or, more preferably, from about −5° to about 25°. Compounds of formula 1 are thermally unstable, and thus the acylation reaction is not conducted at an elevated temperature.

The reaction is conducted, for example, by slowly adding an excess of acylating agent to a mixture of a compound of formula 1 and solvent, and then stirring the resulting reaction mixture at about −20° to about 10° for about 30 minutes to about 1½ hours. The reaction mixture can then be allowed to stir at about room temperature for about one or two days. The mixture can then be recooled to about −20° to about 10° and an additional small amount of solvent and a small amount of a lower alkanol such as ethanol, or more preferably methanol are added.

A compound of formula 2 can be recovered by conventional means such as evaporation of the solvent.

Alternatively, a compound of formula 1 can be protected as acetals, ethers or silyl ethers to yield a compound of formula 2 wherein $R^1$ is lower alkyl, aralkyl, phenyl, substituted phenyl, tri-lower alkylsilyl, di-lower alkylarylsilyl, lower alkyldiarylsilyl, triarylsilyl, or a group of the formula:

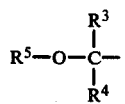

wherein $R^3$ is hydrogen or lower alkyl; $R^4$ and $R^5$ each independently are lower alkyl and $R^4$ and $R^5$ taken together are lower alkylene of from 3 to 6 carbon atoms.

To form acetal protecting groups a compound of formula 1 can be treated with lower alkyl or aromatic vinyl ethers and a catalytic amount of a strong acid such as p-toluenesulfonic acid or hydrochloric acid in an inert solvent such as the ethers, diethyl ether or tetrahydrofuran or inert organic solvents such as benzene, toluene, or methylene chloride at a temperature range of about −50° C. to about 50° C., most preferably about −50° C. to about 0° C. to yield acetal compounds of formula 2.

To form ether protecting groups a compound of formula 1 can be treated with lower alkyl, aralkyl or aryl halide and a tertiary amine or aromatic tertiary amine base in an inert solvent such as benzene, toluene or methylene chloride, an ether solvent such as diethyl ether or tetrahydrofuran or a tertiary amine solvent such as triethylamine or pyridine. Suitable tertiary amine or aromatic tertiary amine bases include triethyl amine, pyridine, s-collidine and 4-dimethylaminopyridine. Suitable lower alkyl halides include methyl iodide, ethyl iodide and the like. Suitable aralkyl halides include benzyl bromide, p-methoxybenzyl chloride, p-nitrobenzyl bromide and the like. Suitable aryl halides include iodobenzene, p-nitrophenyl iodide and the like. The reactions are typically carried out at a temperature range of about −20° C. to about 100° C. to yield ether compounds of formula 2.

To form silyl ether protecting groups a compound of formula 1 can be treated with tri-lower alkylsilyl halides such as trimethylsilyl chloride, trimethylsilyl bromide, and t-butyl dimethylsilyl chloride, di-lower alkyl-arylsilyl halides, such as dimethylphenylsilyl chloride, lower alkyldiarylsilyl halides such as methyldiphenylsilyl chloride, and triarylsilyl halides such as triphenylsilyl iodide and a tertiary amine base such as triethylamine or imidazole or an aromatic tertiary amine base such as pyridine or 4-dimethyl-aminopyridine. Suitable solvents include polar aprotic solvents such as dimethylformamide, inert solvents such as benzene, toluene, and methylene chloride and ether solvents such as diethyl ether and tetrahydrofuran. Suitable temperatures for the reaction are about −20° C. to about 100° C., most preferably about 0° C. to about 50° C. to yield silyl ether compounds of formula 2.

A compound of formula 2 can be converted to a compound of formula 3 by reaction with a dehydrating agent.

The dehydrating agent can be an inorganic acid halide. More particularly, the inorganic acid halide can be a sulfur oxyhalide such as thionyl bromide, or most preferably, thionyl chloride.

The inorganic acid halide can also be a phosphorous oxy halide such as phosphorous oxybromide, or, more preferably, phosphorous oxychloride.

The dehydrating agent can be an organic acid halide. More particularly, the organic acid halide can be a sulfonyl halide such as methanesulfonyl chloride or p-toluenesulfonyl chloride.

The dehydrating agent can alternately be a strong acid such as methanesulfonic acid, p-toluenesulfonic acid, formic acid, boron trifluoride etherate and the like.

Suitable solvents include aromatic hydrocarbons such as benzene, toluene, xylene and the like; and hydrocarbons such as hexane, iso-octane, and the like.

With a sulfur oxyhalide, phosphorous oxyhalide or sulfonyl halide, as the dehydrating agent, a tertiary amine base is required as a co-solvent. Suitable tertiary amines include trialkylamines such as triethylamine, diisopropylethyl amine, and the like. Suitable tertiary amines can also include aromatic tertiary amines such as pyridine, lutidine, s-collidine and the like.

The dehydration reaction is carried out at temperatures in a range of about −10° to about 50°, most preferably in a range of about 0° to about 30°.

A preferred dehydrating agent is thionyl chloride. A preferred solvent system is benzene and pyridine.

The reaction mixture of a compound of formula 2 and a dehydrating agent, is stirred until dehydration is complete.

Recovery of a compound of formula 3 can be by conventional means such as a standard work up and evaporation of solvent.

A compound of formula 3, wherein $R^1$ is

wherein $R^2$ is lower alkyl, aralkyl, phenyl or substituted phenyl, can be converted to a compound of formula 4 by either base saponification or hydride reduction.

Base saponification, can be carried out with an alkaline earth metal hydroxide such as barium hydroxide; or, more preferably, an alkali metal hydroxide, such as sodium hydroxide or potassium hydroxide is used.

The solvent is a lower alkanol such as ethanol, or most preferably methanol. Alternatively, mixtures of alcohol with water as a cosolvent may be used. Optionally, another miscible cosolvent to help solubilize the organic reactants, for example, an ether such as tetrahydrofuran or dimethoxyethane may be used.

The reaction is run at a temperature from about $-20°$ to about $50°$. Most preferably, the reaction is run at a temperature from about $-5°$ to about $20°$.

The reaction is run until deacetylation is complete.

A compound of formula 4 can be recovered by conventional means as by standard workup followed by high pressure liquid chromatography.

A compound of formula 3, wherein $R^1$ is lower alkyl, aralkyl, phenyl, substituted phenyl, tri-lower alkylsilyl, di-lower alkylarylsilyl, lower alkyldiarylsilyl, triarylsilyl or a group of the formula

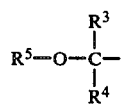

wherein $R^3$ is hydrogen or lower alkyl; $R^4$ and $R^5$ each independently are lower alkyl or $R^4$ and $R^5$ taken together are lower alkylene of from 3 to 6 carbon atoms, can be converted to a compound of formula 4 by reaction with an acid or tri-lower alkylsilyl iodide in an inert solvent, preferably trimethylsilyl iodide in methylene chloride.

25,26-dehydro-1α,24R-dihydroxycholecalciferol, 25,26-dehydro-1α,24S-dihydroxycholecalciferol, and the epimeric mixture are useful in treating osteoporosis, tumors and leukemia. These compounds or an epimeric mixture thereof are also useful in providing vitamin D activity to a host in need of the same.

The activity of 25,26-dehydro-1α,24R-dihydroxycholecalciferol for the treatment of tumors and leukemia was demonstrated by the following test procedures. Subject: Anti-proliferative and differentiation-inducing effects of 25,26-dehydro-1α,24R-dihydroxycholecalciferol

General experimental description

Cultures of HL-60 cells were established in the absence (control) or presence of various concentrations of the test compound. After a 4-day incubation period, the cultures were evaluated for proliferation of tumor cells, tumor cell viability, and cellular differentiation. Proliferation was assessed by directly enumerating the increased number of tumor cells resulting from incubation. Viability was determined by dye exclusion technique to learn whether any of the compounds were lethal to cultured HL-60 cells. Cellular differentiation was evaluated by determining the number of cells which had acquired the enzymes necessary to support a respiratory burst and the functional ability to phagocytose (bind/internalize) particulate material from their environment; both activities being characteristic of mature macrophages and granulocytes,

Methods

Tissure culture medium used in these experiments was RPM1-1640 supplemented prior to use to 10% v/v with fetal bovine serum (heat inactivated at 56° for 30 minutes), to 130 units per ml with penicillin and 130 μg per ml with streptomycin, and to an additional 1.6 millimolar with L-glutamine.

Experimental compounds were dissolved in sufficient ethanol to yield stock solutions of $1 \times 10^{-2}$ molar. Reduced lighting was employed when working with compounds and stock solutions were stored in the dark at $-20°$ in an argon atmosphere. Compounds were diluted with tissue culture medium and added to flasks containing HL-60 cells to achieve the final concentrations described in each experiment.

The promyelocytic (HL-60) tumor cell line was derived from a patient with acute promyelocytic leukemia. HL-60 cells were maintained in liquid culture by serial weekly passage in tissue culture medium. In any experiment, three replicate flasks were incubated without compound (control) or in the presence of varying concentrations of compound. After 4 days of incubation at 37° in a humidified atmosphere of 5% $CO_2$, in air, cultures were evaluated for tumor cell proliferation, viability and differentiation.

Quantitation of proliferation was done by enumerating the number of HL-60 cells in each individual flasks (3 flasks per experimental point) using a model ZBI Coulter Counter. Results are shown as the number of cells per ml of tissue culture medium expressed as the mean±standard deviation and as percent reduction of cell number calculated according to the formula:

$$\left(1 - \frac{\text{mean number of cells in experimental cultures}}{\text{mean number of cells in control cultures}}\right) \times 100.$$

Experimental cultures with the same or slightly greater cell numbers than control cultures are reported as zero percent reduction.

Viability of tumor cells was determined by the method of trypan blue dye exclusion. Cells in tissue culture medium were added to a four-fold larger volume of 0.4% trypan blue in saline. Cells were scored as viable upon microscopic examination if they excluded dye and as dead if they were stained blue. The viability of cells from all experimental cultures was never less than that from control cultures indicating that the compounds tested were not toxic to HL-60 cells in the concentrations employed.

Quantitation of differentiated cells was done by the biochemical method of nitroblue tetrazolium (NBT) reduction. Sufficient cells were pooled from replicate cultures, centrifuged at 220×g, washed once with serum-free tissue culture medium, and resuspended to $1 \times 10^6$ cells per ml in $Ca^{++}$—$Mg^{++}$-deficient phosphate buffered saline (prepared by supplementing $Ca^{++}$—$Mg^{++}$-free phosphate buffered saline (PBS) to 10% v/v with heat-inactivated fetal bovine serum). Nitroblue tetrazolium was dissolved at 1 mg per ml in $Ca^{++}$—$Mg^{++}$-deficient PBS with gentle heating and mixing. Tetradecanoyl phorbol acetate (TPA) was dissolved at 1 mg per ml in ethanol and stored at $-20°$ C. Just prior to use, a working solution of TPA was prepared by diluting the stock concentration 100-fold with $Ca^{++}$—$Mg^{++}$-deficient PBS. The test was done in 12×75 mm tubes by adding 0.5 ml $Ca^{++}$—$Mg^{++}$-deficient PBS, 1.0 ml of HL-60 cells, 0.5 ml of NBT solution, and 0.02 ml of the working TPA solution. After mixing, the tubes were incubated in a 37° water bath for 25 minutes then transferred to ice. Undifferentiated and differentiated cells present in any sample were determined microscopically by surveying 200-400 cells per sample or by cytofluorograph by surveying greater than 30,000 cells. Cells without pigmented granules (clear cells) were judged to be undifferentiated while those containing greater than 3 blue-black formazan granules were scored as differentiated. Generally, differentiated cells were intensely pigmented clearly indicating the enzymatic conversion of NBT to formazan. Results are expressed as the percentage of differentiated cells present in any sample as calculated according to the formula:

$$100 \times \frac{\text{number of formazan positive cells}}{\text{total number of cells counted}}.$$

Quantitation of differentiated HL-60 cells on a functional basis was done by enumerating the number of cells in any sample which had acquired the ability to phagocytose (bind/internalize) particulate material from their environment, a characteristic of mature macrophages and granulocytes. Sufficient cells were pooled from replicate cultures, centrifuged at 200×g, washed once with serum-free tissue culture medium, and resuspended to $1 \times 10^6$ cells per ml in serum-free tissue culture medium. To a 1.0 ml sample in 12×75 mm tubes was added 0.1 ml of a 1:10 dilution from stock of fluorescent microspheres obtained as a gift from Dr. William Dreyer at the California Institute of Technology. Latex beads, yeast cells or red blood cells may also be used in place of fluorescent microsphere in this step. Cells and particle were mixed, incubated for 15 minutes in a 37° water bath, collected in a transfer pipet, and overlayed onto a 5 ml cushion of fetal bovine serum in a 15 ml conical culture tube. After centrifugation at 150×g for 8 minutes, the excess particulate (upper layer) was discarded as was the remainder of the serum cushion leaving only a cell pellet and cell-associated particulate. The resultant pellets were resuspended in 1.0 ml of tissue culture medium containing 10% fetal bovine serum, transferred to a hemacytometer, and evaluated microscopically using both ultraviolet and visible light sources. Undifferentiated and differentiated cells present in any sample were determined microscopically by surveying 200-400 cells per sample. Non-fluorescent cells, identified only by visible light, were judged to be undifferentiated. Generally, differentiated cells were intensely fluorescent clearly indicating extensive phagocytosis of particulate material. Results are expressed as the percentage of differentiated cells present in any sample as calculated according to the formula:

$$100 \times \frac{\text{number of phagocytic cells}}{\text{total number of cells counted}}.$$

Results obtained from using these experimental procedures appear in Tables I, II, III and IV.

TABLE I

ETHANOL, EMPLOYED AS VEHICLE, DOES NOT INHIBIT PROLIFERATION OR INDUCE DIFFERENTIATION OF HL-60 CELLS, IN VITRO

| Expt. Number | Compound and Concentration | Proliferation[a] HL-60 cells per ml × $10^{-4}$ (mean ± SD) | Differentiation[b] formazan "+" cells total cells counted | % "+" |
|---|---|---|---|---|
| I | None (control) | 25.5 ± 2.3 | 3/452 | 1 |
|   | Ethanol (0.01%, v/v) | 26.5 ± 1.2 | 2/427 | 1 |
| II | None (control) | 28.2 ± 0.6 | 1/325 | 1 |
|   | Ethanol (0.01%, v/v) | 28.9 ± 1.4 | 2/371 | 1 |
| III | None (control) | 102.2 ± 5.6 | 2/350 | 1 |
|   | Ethanol (0.10%, v/v) | 101.7 ± 2.3 | 2/383 | 1 |
| IV | None (control) | 140.0 ± 9.3 | 6/337 | 2 |
|   | Ethanol (0.18%, v/v) | 146.0 ± 14.1 | 4/330 | 1 |

[a]The initial HL-60 cell densities employed in these experiments were: in experiments I and II, $1 \times 10^4$ per ml; in experiment III, $2 \times 10^4$ per ml; and in experiment IV, $5 \times 10^4$ per ml. Incubation period in all experiments was 4 days.
[b]Differentiated cells were determined by the method of enzymatic reduction of NBT to formazan and were enumerated by light microscopy.

TABLE II

ANTI-PROLIFERATIVE EFFECTS OF 25,26-DEHYDRO-1α,24R—DIHYDROXYCHOLECALCIFEROL ON HL-60 CELLS, IN VITRO

| Compound and[a] Concentration (× $10^{-9}$ molar) | HL-60 Cells per ml After Varying Periods of Incubation[b,c] | | |
|---|---|---|---|
| | day 3 | day 4 | day 6 |
| None (control) | 10.9 ± 0.4 (0) | 26.4 ± 0.1 (0) | 127.0 ± 5.6 (0) |
| 1α,24R—(OH)$_2$—$\Delta^{25}$-D$_3$ 15 | 12.0 ± 0.2 (0) | 24.1 ± 1.0 (9) | 113.0 ± 1.4 (11) |
| 1α,24R—(OH)$_2$—$\Delta^{25}$-D$_3$ 15 | 12.0 ± 0.5 (0) | 22.0 ± 0.4 (17) | 71.4 ± 1.3 (44) |
| 1α,24R—(OH)$_2$—$\Delta^{25}$-D$_3$ 45 | 12.3 ± 0.2 (0) | 19.0 ± 0.8 (28) | 31.4 ± 0.5 (75) |
| 1α,24R—(OH)$_2$—$\Delta^{25}$-D$_3$ 90 | 11.8 ± 0.1 (0) | 15.4 ± 0.9 (42) | 21.4 ± 1.1 (83) |

[a]The final vehicle concentration in any experimental culture was ≦0.03%, v/v, ethanol.
[b]Triplicate cultures were established with $1 \times 10^4$ cells per ml for each time point; cell density was determined for each culture vessel and results are expressed as mean cell number per ml ± standard deviation (× $10^{-4}$). Numbers in parentheses reflect the percent reduction of cell numbers relative to the appropriate control cultures.
[c]The viability of cells from all cultures was ≧95%.

TABLE III

DIFFERENTIATION-INDUCING EFFECTS OF 25,26-DEHYDRO-1α,24R—DIHYDROXYCHOLECALCIFEROL ON HL-60 CELLS, IN VITRO

| Compound and Concentration (× $10^{-9}$ molar) | Differentiated Cells Present After Varying Periods of Incubation[a] | | | | | |
|---|---|---|---|---|---|---|
| | day 3 | | day 4 | | day 6 | |
| | diff. cells total | % diff. | diff. cells total | % diff. | diff. cells total | % diff. |
| NBT reduction | | | | | | |
| None (control) | 2532/42982 | 6 | 2483/43577 | 6 | 2306/39442 | 6 |
| 1α,24R—(OH)$_2$—$\Delta^{25}$-D$_3$ 5 | 2443/44545 | 5 | 3401/42923 | 8 | 3179/47638 | 7 |
| 1α,24R—(OH)$_2$—$\Delta^{25}$-D$_3$ 15 | 8971/40398 | 22 | 9489/40666 | 23 | 8167/47032 | 17 |
| 1α,24R—(OH)$_2$—$\Delta^{25}$-D$_3$ 45 | 14932/30509 | 49 | 20003/33311 | 60 | 22787/36263 | 63 |

TABLE III-continued

DIFFERENTIATION-INDUCING EFFECTS OF 25,26-DEHYDRO-1α,24R—DIHYDROXYCHOLECALCIFEROL ON HL-60 CELLS, IN VITRO

| Compound and Concentration ($\times 10^{-9}$ molar) | Differentiated Cells Present After Varying Periods of Incubation[a] | | | | | |
|---|---|---|---|---|---|---|
| | day 3 | | day 4 | | day 6 | |
| | diff. cells total | % diff. | diff. cells total | % diff. | diff. cells total | % diff. |
| 1α,24R—(OH)$_2$—$\Delta^{25}$-D$_3$ 90 | 29458/47866 | 62 | 30230/41142 | 73 | 35708/45388 | 79 |
| Phagocytosis | | | | | | |
| None (control) | 7/247 | 3 | 3/301 | 1 | 22/261 | 8 |
| 1α,24R—(OH)$_2$—$\Delta^{25}$-D$_3$ 5 | 24/329 | 7 | 22/223 | 10 | 45/290 | 16 |
| 1α,24R—(OH)$_2$—$\Delta^{25}$-D$_3$ 15 | 76/324 | 24 | 96/332 | 29 | 83/333 | 25 |
| 1α,24R—(OH)$_2$—$\Delta^{25}$-D$_3$ 45 | 174/329 | 53 | 206/296 | 70 | 176/223 | 79 |
| 1α,24R—(OH)$_2$—$\Delta^{25}$-D$_3$ 90 | 181/261 | 69 | 219/255 | 86 | 200/218 | 96 |

[a]Cells pooled from replicate cultures were evaluated for differentiation by cytofluorograph (for NBT) or ultraviolet microscopy (for phagacytosis). For additional details see footnotes to Table II.

Results and Conclusion

Ethanol, employed as vehicle, did not inhibit proliferation or induce differentiation of cultured HL-60 cells. The results of four experiments delineating the impact of ethanol on HL-60 cells are shown in TABLE I. Experiments I and II reveal that ethanol tested at concentrations of 0.01%, v/v, had no effect on the proliferation of HL-60 cells nor was there any effect on their undifferentiated status. Moreover, concentrations of ethanol 10- to 18-fold in excess of those routinely employed in other experiments were similarly ineffective on cultured HL-60 cells as shown in experiments III and IV.

Anti-proliferative and differentiation-inducing effect of 25,26-dehydro-1α,24R-dihydroxycholecalciferol. The data detailed in TABLE II shows the anti-proliferative effect of 25,26-dehydro-1α,24R-dihydroxycholecalciferol and those in TABLE III describe the differentiation-inducing effect of the compound; the information in both tables being derived from the same experiment. As shown in TABLE II, the proliferation of HL-60 cells was inhibited by 25,26-dehydro-1α,24R-dihydroxycholecalciferol in a dose-dependent fashion, was detectable by cell enumeration techniques as early as day 4 of incubation, and a plateau was observed in the dose-response curves indicating complete inhibition of proliferation at doses of 45 to 90×10$^{-9}$ molar. As shown in TABLE III, HL-60 cells were also induced to differentiate into more mature cells at the same doses of compound which inhibited proliferation. Control cultures contained only 6% differentiated cells after 3, 4 and 6 days of incubation when evaluated by the method of NBT reduction. In contrast, cultures containing 5, 15, 45 or 90×10$^{-9}$ molar concentrations of 25,26-dehydro-1α,24R-dihydroxycholecalciferol were observed to contain increasing proportions of differentiated cells at all incubation times. When evaluated for the cellular function of phagocytosis, similar results were obtained: control cultures contained fewer than 8% phagocytic cells while experimental cultures clearly revealed a dose-related increase in the proportion of cells capable of phagocytosis, a characteristic of differentiated macrophages and granulocytes.

25,26-Dehydro-1α,24R-dihydroxycholecalciferol induced cellular differentiation in a dose dependent fashion and possess a potency of 40% of that of 1α,25-dihydroxycholecalciferol. However, the potential for hypercalcemia is much less for 25,26-dehydro-1α,24R-dihydroxycholecalciferol than for 1α,25-dihydroxycholecalciferol as indicated by the antirachitogenic increase in Tibia ash weight in chicks as indicated in Table IV.

TABLE IV

| Substance | Chick Intestinal Cytosol Binding Ratio* | Antirachitogenic Increase in Tibia Ash in Chicks** | HL-60 Test Differentiation NBT Test ED$_{50}$ (nM) |
|---|---|---|---|
| 1α,25-Dihydroxycholecalciferol (Calcitriol) | 1.0 | 61% 27 ng | 12 |
| 25,26-Dehydro-1α,24R—dihydroxycholecalciferol | 4.6 | 20% 300 ng | 30 |

*25,26 Dehydro-1α,24R—dihydroxycholecalciferol and tritium-labelled calcitriol, both in isopropanol, were incubated with chick intestinal cytosol binding protein for 60 minutes at room temperature. Bound $^3$H—calcitriol was separated from unbound $^3$H—calcitriol using polyethylene glycol. The extent of binding was determined by measuring the decrease in binding of $^3$H—calcitriol at each concentration of test compound compared with binding in the absence of test compound. The binding ratio was calculated from the concentration of test compound compared to the concentration of calcitriol which decreased the binding of $^3$H—calcitriol to the cytosol binding protein by 50%. The data from the chick intestinal cytosol binding experiments demonstrate the antirachitogenic properties of the tested compounds.
**One-day-old White Leghorn cockerels were placed on a vitamin D-deficient diet which contained 1% calcium and 0.7% phosphorus and were housed under ultraviolet-free lighting (General Electric F40G0 gold fluorescent lights). The test compound was dissolved in propylene glycol and administered orally in a volume of 0.2 ml/day for 21 consecutive days. Controls were treated with vehicle alone. Chicks were autopsied on the day after the last treatment day.

Compounds of formula 4 can be administered in dosages that are in the range of about 0.1 micrograms to 500 micrograms per day for the treatment of osteoporosis, tumors and leukemia. It will be understood, however, that the dosages indicated above are only given by way of example and that they in no way limit the scope of the use of this invention. The compounds of formula 4 are preferably administered orally but can also be administered subcutaneously, intramuscularly, intravenously, intraperitoneally, or topically.

Compounds of formula 4 can be formulated into compositions such as tablets, capsules, and the like, or elixers for oral administration, or in sterile solutions or suspensions for parenteral administration. About 0.1 micrograms to 500 micrograms of the compounds of formula 4 can be compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent: methyl and propyl parabens a preservative, a dye, and a flavoring such as cherry or orange flavor.

Sterile compositions for injection can be formulated according to conventional pharmaceutical practice by dissolving or suspending the active substance in a vehicle, such as water for injection, a naturally occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

In the Examples which follow, the temperatures are in degrees Celsius unless indicated otherwise. The Examples which follow are further illustrative of the present invention.

EXAMPLE 1

Preparation of 1α,24R,25-trihydroxycholecalciferol 1,3,24-triacetate

To a mixture of 0.100 g of 1α,24R,25-trihydroxycholecalciferol and 10 ml of triethylamine at 0° C. was added slowly 7.6 ml of acetic anhydride and the mixture was stirred at 0° C. for 1 hour and at 23° C. for 29 hours under an argon atmosphere. The mixture was recooled to 0° C. and 10 ml of triethylamine and 10 ml of methanol were added slowly. The mixture was evaporated to dryness to yield 0.128 g of 1α,24R,25-trihydroxycholecalciferol 1,3,24-triacetate. $[α]_D^{22}+9.6°$ (c 0.27, $CHCl_3$).

EXAMPLE 2

Preparation of 1α,24S,25-trihydroxycholecalciferol 1,3,24-triacetate

In a manner analogous to Example 1, 1α,24S,25-trihydroxycholecalciferol is converted to 1α,24S,25-trihydroxy-cholecalciferol 1,3,24-triacetate.

EXAMPLE 3

Preparation of 1α,24R,25-trihydroxycholecalciferol 1,3,24-tris(trimethylsilyl)ether In a manner analogous to Example 1, when 1α,24R,25-trihydroxycholecalciferol is treated with three equivalents of trimethylsilyl chloride in triethylamine, 1α,24R,25-trihydroxycholecalciferol 1,3,24-tris(trimethylsilyl)ether can be obtained.

EXAMPLE 4

Preparation of 1α,24S,25-trihydroxycholecalciferol 1,3,24-tris(trimethylsilyl)ether In a manner analogous to Example 1, 1α,24S,25-trihydroxycholecalciferol is converted to 1α,24S,25-trihydroxycholecalciferol 1,3,24-tris(trimethylsilyl)ether.

EXAMPLE 5

Preparation of 1α,24R,25-trihydroxycholecalciferol 1,3,24-tribenzyl ether

In a manner analogous to Example 1, when 1α,24R,25-trihydroxycholecalciferol is treated with excess benzyl bromide in pyridine, 1α,24R,25-trihydroxycholecalciferol 1,3,24-tribenzyl ether can be obtained.

EXAMPLE 6

Preparation of 1α,24S,25-trihydroxycholecalciferol 1,3,24-tribenzyl ether

In a manner analogous to Example 1, 1α,24S,25-trihydroxycholecalciferol is converted to 1α,24S,25-trihydroxycholecalciferol 1,3,24-tribenzyl ether.

EXAMPLE 7

Preparation of 25,26-dehydro-1α,24R-dihydroxycholecalciferol 1,3,24-triacetate

To a solution of 0.097 g of 1α,24R,25-trihydroxycholecalciferol 1,3,24-triacetate in 4.5 ml of benzene and 3.0 ml of pyridine was added dropwise at 0° C., 1.05 ml of 0.45M thionyl chloride in benzene under an atmosphere of argon. The mixture was stirred at 0° C. for 1 hour and was poured into 20 ml of saturated aqueous sodium bicarbonate solution at 0° C. The product was isolated by extraction with ethyl acetate. The organic phase was washed sequentially with water and saturated brine. The organic phase was then dried over anhydrous magnesium sulfate and filtered. The solution was then evaporated to dryness to yield 0.093 g of 25,26-dehydro-1α,24R-dihydroxycholecalciferol 1,3,24-triacetate. $[α]_D^{23}+5.5°$ (c 0.40, $CHCl_3$).

EXAMPLE 8

Preparation of 25,26-dehydro-1α,24S-dihydroxycholecalciferol 1,3,24-triacetate

In a manner analogous to Example 7, 1α,24S,25-trihydroxycholecalciferol 1,3,24-triacetate is converted to 25,26-dehydro-1α,24S-dihydroxycholecalciferol 1,3,24-triacetate.

EXAMPLE 9

Preparation of 25,26-dehydro-1α,24R-dihydroxycholecalciferol

A solution of 0.094 g of 25,26-dehydro-1α,24R-dihydroxycholecalciferol 1,3,24-triacetate and 11 ml of 1.5% potassium hydroxide in methanol was stirred at 20° C. for 3 hours under an argon atmosphere. The mixture was neutralized to pH 7.5 with glacial acetic acid in water at 0° C. The residue was then partitioned between ethyl acetate and water. The organic phase was washed with saturated brine and dried over anhydrous magnesium sulfate. The mixture was filtered and evaporated to dryness. The residue was purified with a Waters Associates liquid chromatography model 202 using a Whatman M-20 2.2 cm×50 cm, silica gel column and 5:1 ethyl acetate-hexane as eluant to give 0.029 g of pure 25,26-dehydro-1α,24R-dihydroxycholecalciferol, $[α]_D^{23}+58.7°$ (c 0.52, $CH_3OH$).

EXAMPLE 10

Preparation of 25,26-dehydro-1α,24S-dihydroxycholecalciferol

In a manner analogous to Example 9, 25,26-dehydro-1α,24S-dihydroxycholecalciferol 1,3,24-triacetate is converted to 25,26-dehydro-1α,24S-dihydroxycholecalciferol.

In any of the examples of formulations given below 25,26-dehydro-1α,24S-dihydroxycholecalciferol or the mixture of 25,26-dehydro-1α,24(R,S)-dihydroxycholecalciferol may be used in place of the 24R- epimer. For instance, in Example 11, first column on the left, 0.025 mg of the mixture of 25,26-dehydro-1α,24(R,S)-dihydroxycholecalciferol may be used in place of 0.025 mg of the 24R-epimer.

EXAMPLE 11

Tablet Formulation

| | | mg/tablet | |
|---|---|---|---|
| 1. | 25,26-dehydro-1α,24R—dihydroxycholecalciferol | 0.025 | 0.100 | 0.5 |
| 2. | Lactose | 157.975 | 157.900 | 157.500 |
| 3. | Avicel PH 102 | 20.000 | 20.00 | 20.0 |
| 4. | Modified Starch | 20.000 | 20.000 | 20.0 |
| 5. | Magnesium Stearate | 2.000 | 2.000 | 2.0 |
| | Total | 200.000 | 200.000 | 200.000 mg |

Procedure:
1. Mix items 1–4 in a suitable mixer; mill if necessary.
2. Add magnesium stearate and mill.
3. Compress on suitable press.

EXAMPLE 12

Capsule Formulation

| | | | | |
|---|---|---|---|---|
| 1. | 25,26-dehydro-1α,24R—dihydroxycholecalciferol | 0.025 | 0.100 | 0.500 |
| 2. | Lactose | 159.975 | 159.900 | 159.500 |
| 3. | Modified Starch | 20.0 | 20.0 | 20.0 |
| 4. | Talc | 20.0 | 20.0 | 20.0 |
| | Total | 200.000 | 200.000 | 200.000 mg |

Procedure:
1. Dissolve Item 1 in alcohol.
2. Mix items 2 and 3; solution in Step 1 is spread over the mixture. Dry overnight.
3. Screen the drug mixture; Mix with talc.
4. Fill into capsules.

The drug can be dissolved in pharmaceutically acceptable solvents such as alcohol, propylene glycol, glycerine, polyethylene glycol. Surfactants, such as polyethylene glycol sorbitan esters, dioctyl sodium sulfosuccinate, polyoxyethylenepolyoxy propylene copolymer can also be added for solubilization of drug. The preservative also can be added to the formulation for the prevention of microbial growths. Illustrative of such formulations are:

| | mg/capsule | | |
|---|---|---|---|
| 1. 25,26-dehydro-1α,24R—dihydroxycholecalciferol | 0.025 | 0.100 | 0.500 |
| Polyethylene Glycol/400 | 400.0 | 400.0 | 400.0 |
| Butylated Hydroxyanisole | 0.2 | 0.2 | 0.2 |
| Ascorbyl Palmitate | 1.0 | 1.0 | 1.0 |

Dissolve BHA and ascorbyl palmitate in PEG 400. Add 25,26-dehydro-1α,24R-dihydroxycholecalciferol and dissolve under and atmosphere of nitrogen. The liquid is filled into softshell capsules.

| | mg/capsule | | |
|---|---|---|---|
| 2. 25,26-dehydro-1α,24R—dihydroxycholecalciferol | 0.025 | 0.100 | 0.500 |
| Polyethylene Glycol 400 | 200.0 | 200.0 | 200.0 |
| Polysorbate 80 | 200.0 | 200.0 | 200.0 |
| Butylated Hydroxyanisole | 0.2 | 0.2 | 0.2 |
| Ascorbyl Palmitate | 1.0 | 1.0 | 1.0 |
| 3. 25,26-dehydro-1α,24R—dihydroxycholecalciferol | 0.025 | 0.100 | 0.500 |
| Polyethylene Glycol 6000 | 200.0 | 200.0 | 200.00 |
| Polysorbate 60 | 200.0 | 200.0 | 200.0 |
| Butylated Hydroxyanisole | 0.2 | 0.2 | 0.2 |
| Ascorbyl Palmitate | 1.0 | 1.0 | 1.0 |

Warm the mixture of PEG 6000 and Polysorbate 60. Add to it BHA and ascorbyl palmitate. Add 25,26-dehydro-1α,24R-dihydroxycholecalciferol under an atmosphere of nitrogen. Fill into hard-shell capsules.

| | mg/capsule | | |
|---|---|---|---|
| 4. 25,26-dehydro-1α,24R—dihydroxycholecalciferol | 0.025 | 0.100 | 0.500 |
| Polyethylene Glycol 400 | 100.0 | 100.0 | 100.00 |
| Polyethylene Glycol 4000 | 300.0 | 300.0 | 300.0 |
| Butylated Hydroxyanisole | 0.1 | 0.1 | 0.1 |
| Butylated Hydroxytoluene | 0.1 | 0.1 | 0.1 |
| Ascorbyl Palmitate | 1.0 | 1.0 | 1.0 |

Warm a mixture of PEG 400 and PEG 4000. Add BHT and ascorbyl palmitate, dissolve. Add 25,26-dehydro-1α,24R-dihydroxycholecalciferol and dissolved under a stream of nitrogen. Fill into hard-shell capsules.

EXAMPLE 13

Tablet Formulation

| | | mg/capsule | |
|---|---|---|---|
| 1. 25,26-dehydro-1α,24R—dihydroxycholecalciferol | 0.025 | 0.100 | 0.500 |
| 2. Lactose | 157.975 | 157.900 | 157.50 |
| 3. Avicel PH 102 | 20.000 | 20.00 | 20.0 |
| 4. Modified Starch | 20.000 | 20.000 | 20.0 |
| 5. Magnesium Stearate | 2.000 | 2.000 | 2.0 |
| Total | 200.000 | 200.000 | 200.000 mg |

Procedure:
1. Mix items 1–4 in suitable mixer; mill if necessary.
2. Add magnesium stearate and mill.
3. Compress on suitable press.

EXAMPLE 14

Capsule Formulation

| | mg/capsule | | |
|---|---|---|---|
| 1. 25,26-dehydro-1α,24R—dihydroxycholecalciferol | 0.025 | 0.100 | 0.500 |
| 2. Lactose | 159.975 | 159.90 | 159.500 |
| 3. Modified Starch | 20.0 | 20.0 | 20.0 |
| 4. Talc | 2.000 | 2.000 | 2.0 |

-continued

| Capsule Formulation | | | |
|---|---|---|---|
| | mg/capsule | | |
| Total | 200.000 | 200.000 | 200.000 mg |

Procedure:
1. Dissolve Item 1 in alcohol.
2. Mix Items 2 and 3; solution in Step 1 is spread over the mixture. Dry overnight.
3. Screen the drug mixture. Mix with talc.
4. Fill into capsules.

| | mg/capsule | | |
|---|---|---|---|
| 1. 25,26-dehydro-1α,24R—dihydroxycholecalciferol | 0.025 | 0.100 | 0.500 |
| Polyethylene Glycol | 400 | 400.0 | 400.00 |
| Butylated Hydroxyanisole | 0.2 | 0.2 | 0.2 |
| Ascorbyl Palmitate | 1.0 | 1.0 | 1.0 |

Dissolve BHA and ascorbyl palmitate in PEG 4000. Add 25,26-dehydro-1α,24R-dihydroxycholecalciferol under an atmosphere of nitrogen. The liquid is filled into soft-shell capsules.

| | mg/capsule | | |
|---|---|---|---|
| 2. 25,26-dehydro-1α,24R—dihydroxycholecalciferol | 0.025 | 0.100 | 0.500 |
| Polyethylene Glycol 400 | 200 | 200.0 | 200.0 |
| Polyscorbate 80 | 200 | 200.0 | 200.0 |
| Butylated Hydroxyanisole | 0.2 | 0.2 | 0.2 |
| Ascorbyl Palmitate | 1.0 | 1.0 | 1.0 |
| 3. 25,26-dehydro-1α,24R-dihydroxycholecalciferol | 0.025 | 0.100 | 0.500 |
| Polyethylene Glycol 600 | 200 | 200.0 | 200.0 |
| Polyscorbate 60 | 200 | 200.0 | 200.0 |
| Butylated Hydroxyanisole | 0.2 | 0.2 | 0.2 |
| Ascorbyl Palmitate | 1.0 | 1.0 | 1.0 |

Warm the mixture of PEG 600 and Polysorbate 60. Add to it BHA and ascorbyl palmitate. Add 25,26-dehydro-1α,24R-dihydroxycholecalciferol under an atmosphere of nitrogen. Fill into hard-shell capsules.

| | mg/capsule | | |
|---|---|---|---|
| 4. 25,26-dehydro-1α,24R—dihydroxycholecalciferol | 0.025 | 0.100 | 0.500 |
| Polyethylene Glycol 400 | 100 | 100.0 | 100.0 |
| Polyethylene Glycol 4000 | 300 | 300.0 | 300.0 |
| Butylated Hydroxyanisole | 0.1 | 0.1 | 0.1 |
| Butylated Hydroxytoluene | 0.1 | 0.1 | 0.1 |
| Ascorbyl Palmitate | 1.0 | 1.0 | 1.0 |

Warm a mixture of PEG 400 and PEG 4000. Add BHT and ascorbyl palmitate, dissolve. Add 25,26-dehydro-1α,24R-dihydroxycholecalciferol and dissolve under a stream of nitrogen. Fill into hard-shell capsules.

We claim:

1. A compound 25,26-dehydro-1α,24R-dihydroxycholecalciferol, its 24S-epimer or an epimeric mixture thereof.

2. The compound in accordance with claim 1, 25,26-dehydro-1α,24R-dihydroxycholecalciferol.

3. A method for treating tumors which comprises administering to a host in need of the same a therapeutically effective amount of 25,26-dehydro-1α,24R-dihydroxycholecalciferol, its 24S-epimer or an epimeric mixture thereof.

4. A method for providing vitamin D activity to a host in need of the same which method comprises administering to such host 25,26-dehydro-1α,24R-dihydroxycholecalciferol, the 24S-epimer, or an epimeric mixture thereof.

5. A pharmaceutical composition comprising an effective amount of a compound 25,26-dehydro-1α,24R-dihydroxycholecalciferol, its 24S-epimer, or an epimeric mixture thereof and an inert pharmaceutical carrier material.

6. A composition in accordance with claim 5 wherein the compound is 25,26-dehydro-1α,24R-dihydroxycholecalciferol.

7. A compound of the formula:

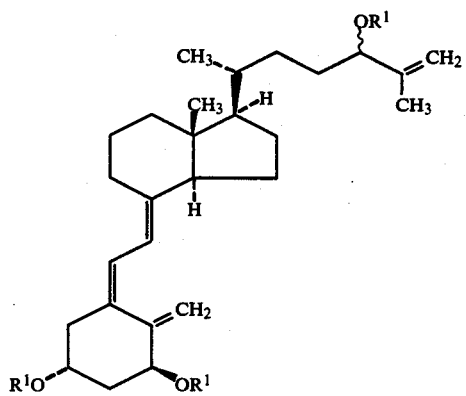

wherein $R^1$ is

wherein $R^2$ is lower alkyl, aralkyl, phenyl, substituted phenyl; or $R^1$ is tri-lower alkylsilyl, di-lower alkylarylsilyl, lower alkyldiarylsilyl, triarylsilyl or a group of the formula

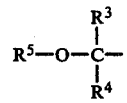

wherein $R^3$ is hydrogen or lower alkyl; $R^4$ and $R^5$ each independently are lower alkyl or $R^4$ and $R^5$ together are a lower alkylene of from 3 to 6 carbon atoms; the 24S epimer, or an epimeric mixture thereof.

8. A compound in accordance with claim 7, wherein $R^1$ is

wherein $R^2$ is lower alkyl, aralkyl, phenyl or substituted phenyl.

9. A compound in accordance with claim 7, wherein $R^1$ is tri-lower alkylsilyl, di-lower alkylarylsilyl, lower alkyldiarylsilyl, or triarylsilyl.

10. A compound in accordance with claim 7, wherein $R^1$ is a group of the formula

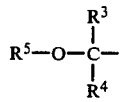

wherein $R^3$ is hydrogen or lower alkyl; $R^4$ and $R^5$ each independently are lower alkyl or $R^4$ or $R^5$ taken together are lower alkylene of from 3 to 6 carbon atoms.

11. A compound in accordance with claim 7, 25,26-dehydro-1α,24R-dihydroxycholecalciferol 1,3,24-triacetate, its 24S-epimer, or the epimeric mixture thereof.

12. The compound in accordance with claim 7, 25,26-dehydro-1α,24R-dihydroxycholecalciferol 1,3,24-triacetate.

* * * * *